(12) United States Patent
Gilboa

(10) Patent No.: US 7,969,143 B2
(45) Date of Patent: Jun. 28, 2011

(54) METHOD OF TRACKING AN OBJECT HAVING A PASSIVE TRANSPONDER ATTACHED THERETO

(75) Inventor: Pinhas Gilboa, Haifa (IL)

(73) Assignee: superDimension, Ltd., Herzliya (IL)

( * ) Notice: Subject to any disclaimer, the term of this patent is extended or adjusted under 35 U.S.C. 154(b) by 0 days.

(21) Appl. No.: 09/860,484

(22) Filed: May 21, 2001

(65) Prior Publication Data

US 2001/0038354 A1 Nov. 8, 2001

Related U.S. Application Data

(63) Continuation of application No. 09/367,318, filed as application No. PCT/IL97/00054 on Feb. 13, 1997, now Pat. No. 6,380,732.

(30) Foreign Application Priority Data

Feb. 13, 1998 (WO) .......................... PCT/97/00054

(51) Int. Cl.
*G01B 7/14* (2006.01)
*G01B 7/30* (2006.01)
(52) U.S. Cl. .................................. 324/207.17; 342/450
(58) Field of Classification Search ............. 324/207.17, 324/207.23, 207.22, 244, 245; 702/153, 702/150, 152; 342/450, 451, 463, 448
See application file for complete search history.

(56) References Cited

U.S. PATENT DOCUMENTS

| 4,135,184 | A | | 1/1979 | Pruzick |
|---|---|---|---|---|
| 4,249,167 | A | | 2/1981 | Purinton et al. |
| 4,287,809 | A | | 9/1981 | Egli et al. |
| 4,308,530 | A | | 12/1981 | Kip et al. |
| 4,425,511 | A | | 1/1984 | Brosh |
| 4,642,786 | A | | 2/1987 | Hansen |
| 4,704,602 | A | | 11/1987 | Asbrink |
| 4,849,692 | A | | 7/1989 | Blood |
| 5,262,722 | A | | 11/1993 | Hedengren et al. |
| 5,493,517 | A | | 2/1996 | Frazier |
| 5,600,330 | A | * | 2/1997 | BLood .......................... 342/463 |
| 6,188,355 | B1 | * | 2/2001 | Gilboa .......................... 342/448 |

FOREIGN PATENT DOCUMENTS

WO IL97/00054 2/1997

\* cited by examiner

*Primary Examiner* — Edward Lefkowitz
*Assistant Examiner* — Subhash Zaveri
(74) *Attorney, Agent, or Firm* — Inskeep IP Group, Inc.

(57) ABSTRACT

A method of tracking translation and rotation of one or more objects within a region of interest. The method includes providing a passive transponder in the region of interest, the transponder having a position and an orientation, generating an electromagnetic field in the region of interest, causing the transponder to generate electromagnetic signal, mapping the electromagnetic field and the signal as functions of the position and the orientation of the transponder, fixing the transponder to the object being tracked, receiving the signals generated by the transponder while the transponder is fixed to the object being tracked, and processing the signal, with reference to the functions, to compute the three-dimensional translational position and three-axis rotational orientation of the object.

2 Claims, 15 Drawing Sheets

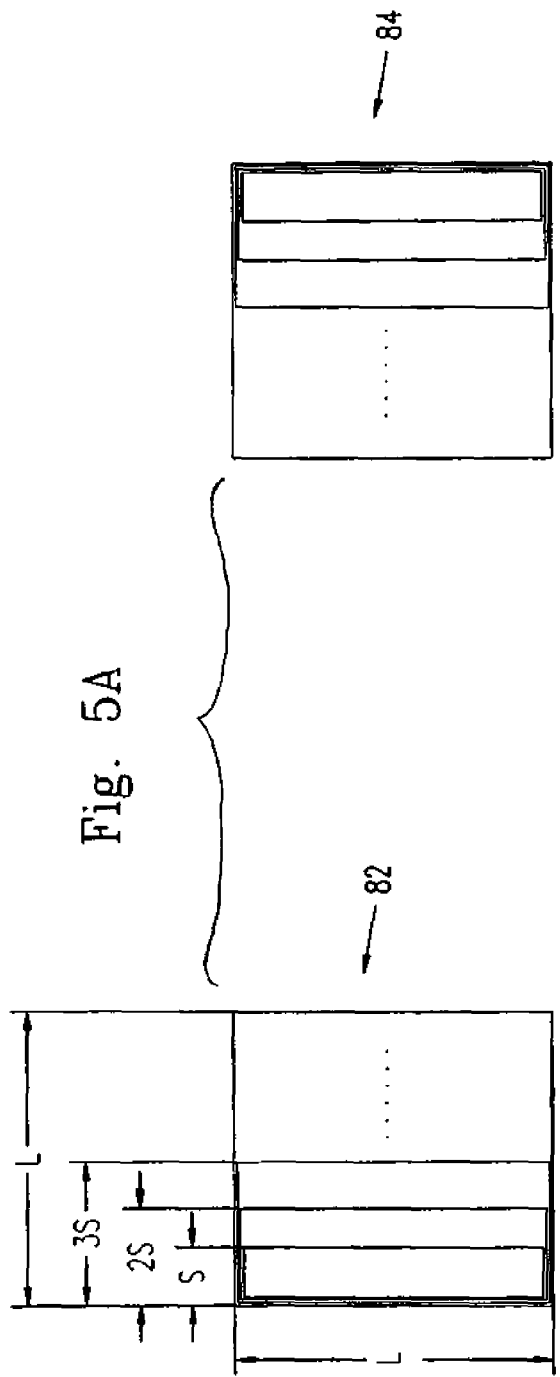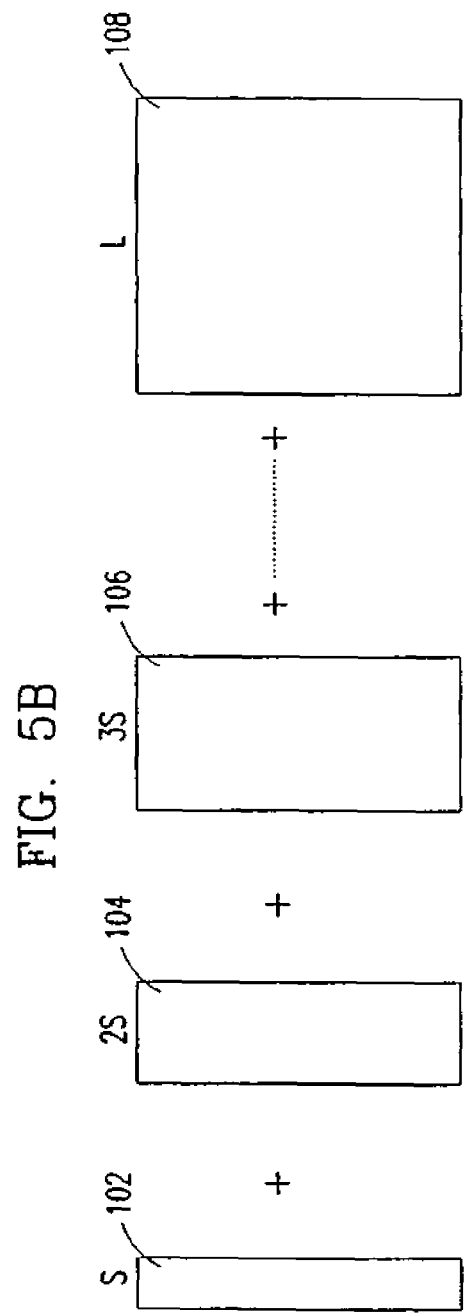

T1

T2

INPUT SIGNAL

AMPLIFIED SIGNAL

METHOD OF TRACKING AN OBJECT HAVING A PASSIVE TRANSPONDER ATTACHED THERETO

This application is a continuation of Ser. No. 09/367,318 filed Jul. 11, 1999 now U.S. Pat. No. 6,380,732, which is a 371 PCT/IL97/00054 filed Feb. 13, 1997.

FIELD OF THE INVENTION

The present invention relates generally to object tracking systems, and specifically to non-contact, electromagnetic methods and devices for tracking the position and orientation of one or more multiple objects.

BACKGROUND OF THE INVENTION

Non-contact electromagnetic tracking systems are well known in the art, with a wide range of applications.

Non-contact tracking systems have been described based on electromagnetic, optical and sonographic detection methods. In many applications, electromagnetic tracking is preferred, because unlike other methods, there need not be a clear line of sight between the object and the detectors. Electromagnetic tracking can also be made relatively immune to interference from background signals, thus avoiding problems such as those caused by stray light in optical systems. Furthermore, the components required for electromagnetic tracking are easily produced and inexpensive.

Exemplary prior art patents for electromagnetic tracking systems include U.S. Pat. Nos. 3,046,228 and 3,121,228, which describe a tracking system for measuring the position of an object in a plane. This system uses two orthogonal coils to generate a rotating dipole field in the vicinity of the object, thereby causing electrical currents to flow in two orthogonal sensor coils. Measurement of the sensor coil current signal is used to determine the object's position.

U.S. Pat. Nos. 3,868,565, 3,983,474 and 4,017,858 describe a tracking system using three orthogonal coils to generate a dipole field, which nutates around a direction vector. The object's position is determined by measuring the current signals generated in three orthogonal sensor coils.

U.S. Pat. No. 4,054,881 describes a tracking system using three coils to generate electromagnetic fields in the vicinity of the object. The fields generated by these three coils are distinguished from one another by open loop multiplexing of time, frequency or phase. The signal currents flowing in three orthogonal sensor coils are used to determine the object's position, based on an iterative method of computation.

U.S. Pat. No. 4,314,251 describes a variation on the '881 patent, wherein only five coils are needed in total, and a non-iterative method of computing is used.

U.S. Pat. No. 4,287,809 describes a tracking system with two or more coils to generate electromagnetic fields, using time multiplexing to distinguish between them. Three orthogonal sensor coils are used to determine the object's position.

Finally, U.S. Pat. No. 4,849,692 describes a tracking system with three orthogonal coils to generate periodic DC electromagnetic fields. A receiver measures the DC field at the object to determine its position.

It would be desirable to provide an electromagnetic tracking method whereby the object or objects being tracked have no physical connection to the surroundings. Desirably, such a method would require that only passive components be mounted on the object, and the object's motion would be unrestricted within the field of detection. All power, active components and additional signals conveyed from the transmitter to the sensor and signal processing circuits would preferably be restricted to the fixed portion of the tracking system.

SUMMARY OF THE INVENTION

The present invention seeks to provide a new, non-contact method for tracking the six-dimensional position and orientation of an object, which may move and rotate relative to an external frame of reference (translation along and rotation about three orthogonal axes) within a region of interest. The method may be used to track a single object or multiple objects simultaneously in a single system.

In a preferred embodiment of the present invention a transponder is mounted on or inside the object to be tracked. One or more electromagnetic field generators, which are fixed in the external reference frame, generate electromagnetic fields in the vicinity of the object. The field generators' electromagnetic fields cause the transponder to generate electromagnetic signals, which are detected by one or more electromagnetic sensors, which are fixed in the external reference frame. Sensor circuits are provided, which determine the six-dimensional position and orientation of the transponder in relation to the external reference frame, using the signals received by the sensors.

In a preferred embodiment of the present invention, the transponder comprises three coils, which define three independent axes and are preferably orthogonal. The transponder coils are coupled to respective electrical circuits, which generate electromagnetic signals with different, characteristic frequencies when excited.

Furthermore, in a preferred embodiment of the present invention, the three coils in the transponder are wound around a common center, preferably a ferromagnetic core. It will be appreciated, however, that the axes of the transponder may be defined by other means, such as antennae, that are capable of receiving and transmitting electromagnetic fields with a preferred direction. Other aspects of the present invention described herein in relation to transponder coils may equally be applied to transponder antennae of other types.

In a preferred embodiment of the present invention, the electrical circuits in the transponder are passive resonant circuits. These resonant circuits may be formed by connecting each of the transponder coils to a respective capacitor, the capacitors being chosen so that each of the circuits thus formed has a different, known resonant frequency. The electromagnetic field generators generate time-varying fields, having components at the resonant frequencies of the transponder circuits, which cause these circuits to resonate. The signal generated by each of the coils may then be identified and distinguished from other signals by its respective resonant frequency.

Another preferred embodiment of the present invention provides that multiple objects, each with its own transponder, may be tracked simultaneously without confusion, providing that every one of the coils in the various transponders to be tracked is coupled to an electrical circuit having a unique, known resonant frequency.

In a preferred embodiment of the present invention, the electromagnetic field generators and sensors comprise coils which are coupled to appropriate electrical source and sensor circuits, respectively. More generally, however, field generation and/or sensing may be accomplished by other types of antennae, which are known in the art. Other aspects of the present invention described herein in relation to field generator and sensor coils may equally be applied to field generator and sensor antennae of other types.

Preferred embodiments of the present invention provide that a total of only four field generator and sensor coils be used. One such embodiment uses three field generator coils and one sensor coil; another such embodiment uses one field generator coil and three sensor coils; and still another such embodiment uses two field generator coils and two sensor coils. Such embodiments can be used to track six degrees of motion of one or multiple objects. Other preferred embodiments may have a total of five, six or more field generator and sensor coils. Where more than four sensors are used, the additional sensors provide redundancy and improved signal-to-noise ratio.

In a preferred embodiment of the invention, one or more coils may function as both electromagnetic field generators and sensors. In this embodiment, both source and sensor circuits are coupled to the coil. Source circuits provide an electrical pulse to the coil, or else the source electrical current to the coil is rapidly switched off or on. Sensor circuits then detect the electromagnetic signals that are subsequently generated by the transponder and received by the sensors.

In preferred embodiments of the present invention, field generator and sensor coils or antennae are formed of different coils, preferably constructed according to prescribed geometrical criteria, so that the signal levels received by the sensor coils remain within a limited, prescribed range, independent of the position of the transponder within the region of interest. Such embodiments permit the sensor circuits to determine the position and orientation of the transponders with equal accuracy and without ambiguity throughout the region of interest.

Source circuits used to drive the field generators may provide continuous or pulsed alternating current signals at the resonant frequencies of the transponders. The sensor circuits then receive signals from both the field generators and the transponders. These signals can be easily distinguished, however, since they are 90° out of phase. It should be understood in this regard that a single field generator may be driven by a multi-frequency signal.

One aspect of preferred embodiments of the present invention, having two or three field generator coils, is that the signal processing and computation circuits are capable of distinguishing among the signals generated by the transponder coils in response to the respective field generator coils. Where pulsed sources are used, each of the field generator coils is coupled to a respective pulse generating circuit, and these circuits are mutually timed so that pulses are applied to each of the coils in sequence, at known, mutually exclusive, times. The sensor circuits are synchronized with the times of the pulses, so that they receive and process signals generated by the transponders synchronously with the field generator pulses. The sensor circuits thus differentiate between signals received from the transponders according to the sequence of applying pulses to the respective field generator coils. In order to allow for more continuous monitoring, however, in a preferred embodiment of the invention, only one field generator is used and at least three sensors are used.

In accordance with preferred embodiments of the present invention, the sensor circuits comprise signal processing and computation circuits, coupled to the sensor coils, which determine the three-dimensional position and three-dimensional rotational orientation of the transponder or transponders, based on the signals received by the sensor coils. The signals received by the sensor coils are typically amplified and then separated into their respective frequency components, by filtering methods known in the art, so as to distinguish between the respective signal amplitudes (and phases, where appropriate) received from the transponder coils.

A preferred embodiment of the present invention further provides computational circuitry, which applies one or more matrix transformations to the measured signal amplitudes so as to compute the position and/or rotational orientation of the transponder. Other mathematical operations, which are known per se in the art, may also be used to compute the transponder's position and/or orientation.

The transponders of the present invention may also be attached to game pieces or toy figures for use in interactive computer games, such as those described in PCT patent application number PCT/US95/10096, filed Jul. 25, 1995, and titled "Computerized Game Board," which is incorporated herein by reference.

Transponders in accordance with the present invention may also be fastened to a person's hand or to movable control objects, for use in actuating remote systems by sensing the motion of the hand or control objects.

The present invention may be usefully applied to cockpit avionics systems, in which the position of the pilot's helmet is tracked in relation to the cockpit in order to appropriately adjust a helmet-mounted display or weapons sighting apparatus.

In a similar application, the transponder of the present invention may be coupled to a helmet or other head-mounted apparatus to provide a determination of the position and orientation of the head for use in virtual reality displays, simulation training and games.

It will be appreciated that these applications are presented here only by way of example, and that the present invention will be useful in a wide range of other applications.

BRIEF DESCRIPTION OF THE DRAWINGS

The present invention will be understood and appreciated more fully from the following detailed description, taken in conjunction with the drawings, in which:

FIG. 5A is a schematic illustration of two sensor array useful in accordance with the preferred embodiment of the present invention shown in FIG. 4;

FIG. 5B is an exploded, explanatory illustration showing the construction of the sensor array of FIG. 5A;

DETAILED DESCRIPTION OF PREFERRED EMBODIMENTS

Figure 1:
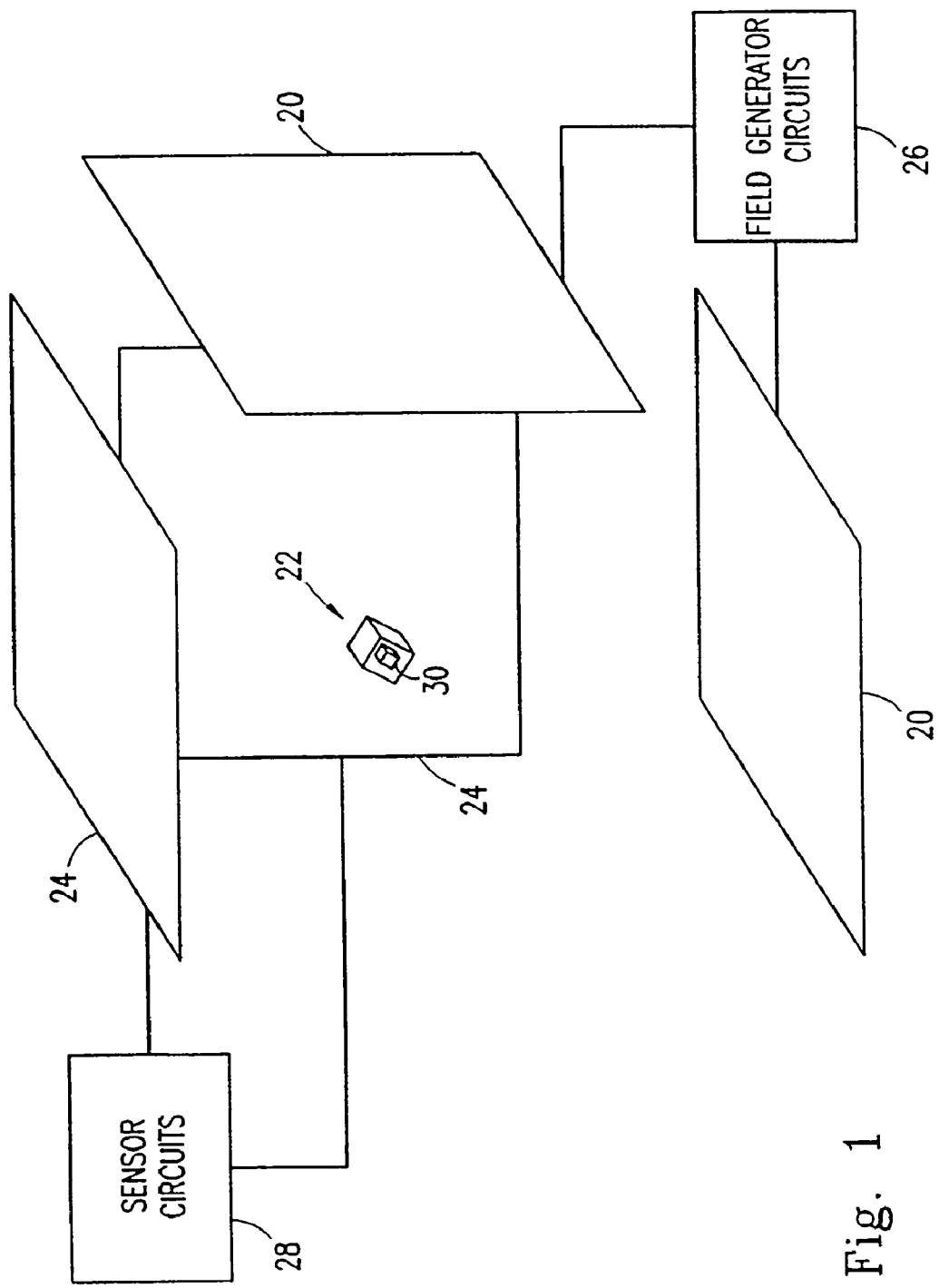
FIG. 1 is a schematic illustration of a general preferred embodiment of the present invention.

Reference is now made to FIG. 1, which illustrates schematically a preferred embodiment of the present invention, comprising electromagnetic field generators 20, freely moving object 22 and sensors 24. Field generators 20 are coupled to field generator source circuits 26; similarly, sensors 24 are coupled to sensor circuits 28. A transponder 30 is mounted inside or on the surface of object 22. Object 22 is free to rotate about any of its axes and move anywhere within a region of interest, in the presence of electromagnetic fields generated by field generators 20.

For simplicity, FIG. 1 shows two field generators 20, fixed at right angles to one another, and two sensors 24, similarly fixed at right angles to one another. It will be appreciated, however, that in preferred embodiments of the present invention, one, two, three or more field generators 20 may be used, and similarly, one, two, three or more sensors 24 may be used. Field generators 20 and sensors 24 may be fixed in any desired mutual orientations. The only requirement is that no two field generators or sensors be identical.

In operation, field generators 20 generate electromagnetic fields in a region of interest. In response to these electromagnetic fields, transponder 30 generates electromagnetic signals, in the form of electromagnetic fields, which are detected by sensors 24. These signals are analyzed by sensor circuits 28 so as to determine the three-dimensional translational position and three-dimensional rotational orientation of the object.

Figure 2:
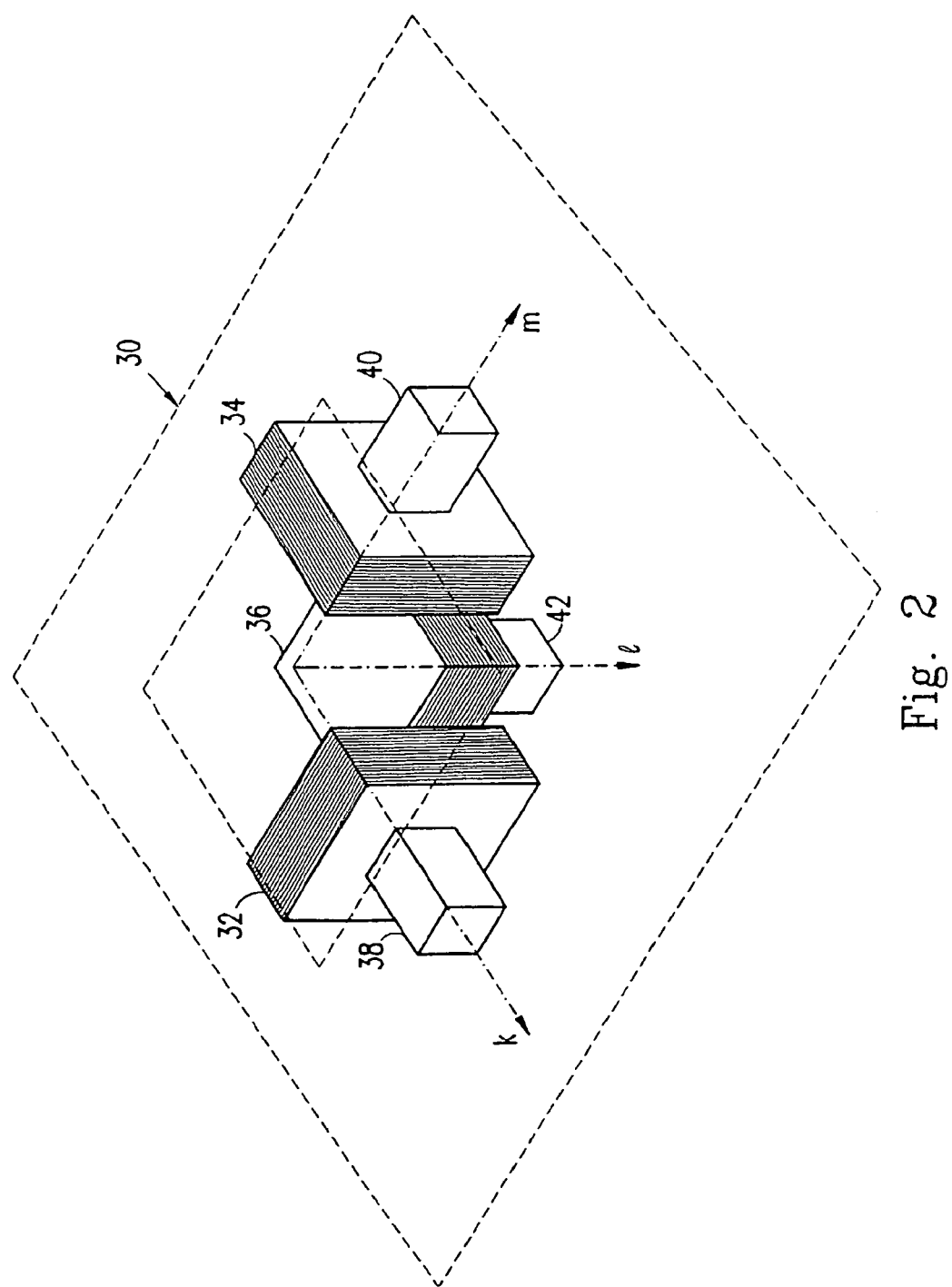
FIG. 2 is a schematic illustration of a transponder in accordance with preferred embodiments of the present invention.

FIG. 2 shows a preferred embodiment of transponder 30, comprising three coils 32, 34 and 36, mutually oriented so as to define respective k, l and m axes in the frame of reference of object 22, to which they are fixed. As FIG. 2 shows, the coils are preferably mutually orthogonal, because this configuration generally allows the position and orientation of the transponder to be determined with the greatest accuracy. It will be appreciated that in some embodiments of the invention, however, these coils may be oriented in whatever directions are convenient, so long as the axes of the coils define a set of linearly independent directions, so that a unique set of Cartesian axes k,l,m may be thereby defined.

Coils 32, 34 and 36 are coupled to electrical circuits 38, 40 and 42, respectively. The coils function as antennas, receiving electromagnetic energy from the fields generated by field generators 20, and conveying this energy to circuits 38, 40 and 42. Each of these circuits responds by generating signal currents, which flow through coils 32, 34 and 36. The coils then function as antennas to transmit these signals, in the form of electromagnetic fields, which are received by sensors 24.

In essence, the circuits formed by the respective coils and capacitors are driven by the electromagnetic fields generated by the field generators. The current in the coils, which is either continuous or decaying, depending on the form of the electromagnetic fields, generates a signal electromagnetic field, which is detected by the sensors.

In a preferred embodiment of the present invention, each circuit 38, 40 and 42 generates signals with a different characteristic frequency. Thus, when these signals are received by sensors 24, it is possible for sensor circuits 28 to distinguish them one from another on the basis of their frequencies.

Preferably the amplitude of the signal generated in each of coils 32, 34 and 36 by circuits 38, 40 and 42 is proportional to the amplitude of a component of the electromagnetic vector field $\underline{h}$ produced by field generators 20 along the axis of the respective coil. Similarly, the response of sensors 24 to the signal fields generated by transponder coils 32, 34 and 36 is preferably a linear function of the vector amplitudes of the signals, which may be described by a vector field r. For the sake of clarity, we note that there is an electromagnetic vector field $\underline{h}_i$ produced by each one of multiple field generators 20, and a response vector field $\underline{r}_j$ relating to each sensor 24.

Transponder coils 32, 34, and 36 define a coordinate system, with axes marked k,l, and m in FIG. 2, which translates and rotates according to the translation and rotation of object 22 relative to the external frame of reference. The translation of the moving coordinate frame, k,l,m, relative to the fixed coordinate frame, which we shall refer to as x,y,z, may be determined using the methods which will be described with reference to equation (4), below.

Rotation of the k,l,m coordinate frame with respect to the x,y,z frame may generally be described by methods known per se in the art as a 3 by 3 Euler transformation matrix T. The signal S received by each one of n sensors 24 and detected by sensor circuits 28 may be separated into k,l and m components, $s^k$, $s^l$ and $s^m$ (in accordance with their frequencies), corresponding respectively to the signals generated by transponder coils 32, 34 and 36, according to the matrix transformations:

$$s_{ij}^k = p\underline{r}_j T^t d_k T \underline{h}_i \quad d_k = \begin{pmatrix} 100 \\ 000 \\ 000 \end{pmatrix} \quad (1)$$

$$s_{ij}^l = p\underline{r}_j T^t d_l T \underline{h}_i \quad d_l = \begin{pmatrix} 000 \\ 010 \\ 000 \end{pmatrix}$$

$$s_{ij}^m = p\underline{r}_j T^t d_m T \underline{h}_i \quad d_m = \begin{pmatrix} 000 \\ 000 \\ 001 \end{pmatrix}$$

where p is a constant characteristic of the system. The n sets of equations (1) may be solved using methods known in the art to find all the elements of matrix T, and thereby fully determine the rotational orientation of the k,l,m axes fixed to object 30, relative to x,y,z axes in the fixed coordinate frame, given that the x,y,z position of the transponder is known from equation (4) if the values of r and h are known.

In a preferred embodiment of the invention, $\underline{r}$ and $\underline{h}$ may be mapped as a function of the transponder position and orientation for each of the field generators 20 and sensors 24, and stored in polynomial or other numerical form. In a preferred method of mapping r and h, transponder 30 is held in a fixed, known x,y,z position and orientation within the region of interest. An electromagnetic field is generated by one of field generators 20, thereby causing a voltage to be developed in transponder coils 32, 34 and 36. The voltage in the transponder coils is measured and used to determine the vector components of $\underline{h}_i$ at the position of the transponder, using methods known in the art. The signals received from the transponder by sensors 24 are similarly measured and used to determine a respective non-normalized response vector $\underline{r}_j'$ for each of the sensors at the given x,y,z location of the transponder. The response vectors for all the sensors are then normalized to the measured voltage to determine respective $\underline{r}_j$ vectors for all of them.

This measurement is made for the full range of x, y and z, preferably by measuring the signals as the transponder is moved from one known location to another within the region of interest, while the rotational orientation of the transponder is kept constant.

In an alternative preferred method of mapping $\underline{r}$ and $\underline{h}$, transponder 30 is held in a fixed, known x,y,z position and orientation within the region of interest. Field generator circuits 26 are disconnected from field generators 20, or are otherwise inactivated. Sensor circuits are temporarily connected to field generators 20, as well as to sensors 24. Electromagnetic signals are generated by transponder coils 32, 34 and 36, by coupling active current-generating circuits, of types known in the art, to the coils. The signals received from the transponder by sensors 24 and by field generators 20 are measured and used to determine respective non-normalized vectors $\underline{h}_i'$ for each of the field generators and $\underline{r}_j'$ for each of the sensors at the given x,y,z location of the transponder. The electromagnetic field vectors for all the field generators and response vectors for all the sensors are then normalized to the transponder drive current to determine respective $\underline{h}_i$ and $\underline{r}_j$ vectors for all of them.

Once $\underline{h}$ and $\underline{r}$ vector fields have been mapped in the region of interest, the constant p in equation (1) may be determined by operating the tracking system to measure the signals $s^k$, $s^l$ and $s^m$, while the transponder is held in a known location. p is then calculated by inserting the measured values of S, $\underline{r}$ and $\underline{h}$ in equation (4), below.

In alternative embodiments of the invention, $\underline{r}$ and $\underline{h}$ are calculated theoretically, based on the geometrical and electrical characteristics of electromagnetic field generators 20 and sensors 24.

In other preferred embodiments of the invention having three or more sensors 24, $\underline{r}$ and $\underline{h}$ may be mapped as functions of the signals $S_j$ due to the respective sensors, rather than in terms of x, y and z coordinates, using the relationships:

$$\underline{r} = f_r(S_1 \ldots S_n)$$

$$\underline{h} = f_h(S_1 \ldots S_n) \quad (2)$$

Coordinates x, y and z may also be mapped as single-valued functions of the sensor signals $S_1$ to $S_n$:

$$\begin{pmatrix} x \\ y \\ z \end{pmatrix} = f_{xyz}(S_l \ldots S_n) \quad (3)$$

The functions $f_r$, $f_h$ and $f_{xyz}$ may be stored in polynomial or other numerical form. Maps generated according to equations (2) and (3) may then be used in operation of the tracking system to determine the transponder's rotational orientation and translational position.

To determine the translational position of the transponder, signals received from the k,l,m transponder coils 32, 34, 36 are summed, in accordance with equation (1):

$$S = s^k + s^l + s^m = p\underline{r}T^i(d_k + d_l + d_m)T\underline{h} = p\underline{r}T^iT\underline{h} \quad (4)$$
$$= p\underline{r} \cdot \underline{h}$$

The sum of signals $s^k$, $s^l$ and $s^m$, S, is thus invariant to rotations of the transponder, and is a function only of its translational position. In preferred embodiments of the present invention, $\underline{r}$ and $\underline{h}$ have been determined either theoretically or empirically, using equation (2), throughout the region of interest for at least four field generator and sensor coils, which give at least three generator-sensor coil pairs. Sensor circuits 28 determine a value S for each such pair, and three such values are used by the computer to calculate the translational position of the transponder in accordance with equation (4).

Figure 3:
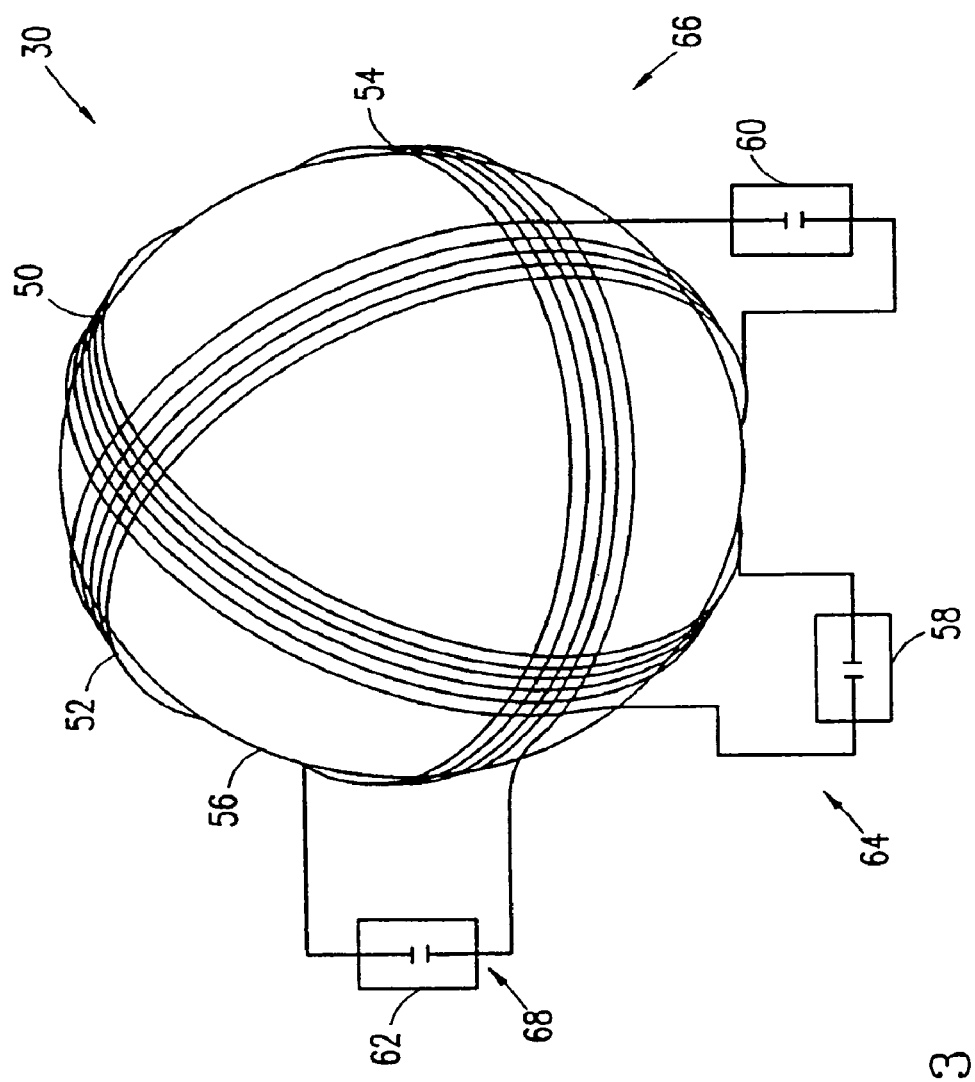
FIG. 3 is a schematic illustration of a preferred transponder in accordance with preferred embodiments of the present invention.

FIG. 3 shows a preferred embodiment of transponder 30, in which three inductive coils 50, 52 and 54 are wound around a common ferromagnetic core 56. The arrangement of the coils in this embodiment defines the origin and orthogonal axes of the k,l,m coordinate system. In other preferred embodiments of the present invention, however, other coil designs or antennas of other types known in the art may be used in place of the coils, providing that these coils or antennas define a k,l,m coordinate system that is fixed with respect to the object, and that these coils or antennas generate signals that can be used to determine the position and orientation of the k,l,m coordinate system relative to the fixed x,y,z axes. While preferred embodiments of the present invention will be described below with reference to the transponder shown in FIG. 3, it will be appreciated that other embodiments of the transponder, with antennae of other types, could equally be used.

Although FIG. 3 shows core 56 as being spherical, in other preferred embodiments the core may be square, rectangular or some other shape. Preferably, however, the inductances of the coils 50, 52 and 54 are equal, so that the responses of the coils to a given electromagnetic field component will be the same.

In the preferred embodiment of the present invention shown in FIG. 3, each of coils 50, 52 and 54 is connected to a respective capacitor 58, 60 and 62. The inductive coils together their respective capacitors form resonant circuits 64, 66 and 68, with characteristic frequencies, $\omega_k$, $\omega_l$, and $\omega_m$, determined by the values of inductance, capacitance and resistance in the circuits. Capacitors 58, 60 and 62 preferably have different values of capacitance, so that each of the circuits resonates at a different frequency.

In a preferred embodiment of the present invention, electromagnetic field generators 20 generate time-varying fields, having frequency components at the resonant frequencies $\omega_k$, $\omega_l$, and $\omega_m$ of circuits 64, 66 and 68. The circuits are excited by these fields and consequently resonate at their respective frequencies, thereby generating signals at these resonant frequencies, which are received by sensors 24. Sensor circuits 28 separate these signals according to frequency, so that the signal amplitude due to each of the coils 50, 52 and 54 can be determined.

In some preferred embodiments of the present invention, multiple objects may be tracked simultaneously within the region of interest, using the same electromagnetic field generators and sensors. In these embodiments, each object to be tracked is provided with a transponder according to one of the preferred embodiments described above in reference to FIGS. 2 and 3. In a preferred embodiment, using transponders 30 as shown in FIG. 3, capacitor 58, 60 and 62 are provided for each of the transponders, with values of capacitance selected so that the resonant frequencies $\omega_k^{(l)}$, $\omega_l^{(i)}$, and $\omega_m^{(l)}$ of the coils of the lth transponder are different from the resonant frequencies of all other transponders with in the region of interest. Sensor circuits 28 distinguish the signal amplitudes at each of the frequencies, so that signal values $s^{k(l)}$, $s^{i(l)}$ and $s^{m(l)}$ may be determined independently for each of the objects. Equations (1) are then used to find the position and orientation matrix T independently for each of the objects.

In a preferred embodiment of the present invention, the electromagnetic field generators and sensors comprise coils, which act as antennae to generate electromagnetic fields and receive electromagnetic signals, respectively, within the region of interest. More generally, however, in alternative embodiments of the invention, other types of antennae that are known in the art may be used for these purposes. Other aspects of the present invention, which will be described herein in relation to field generator and sensor coils, may equally be applied to field generator and sensor antennae of other types.

Each electromagnetic field generator 20 is characterized by its own excitation field h, which is a function of the position, orientation and geometric configuration of the field generator coil and antenna. Similarly, each of the sensors 20 is characterized by its own response field r, which is a function of the position, orientation and geometric configuration of the sensor coil or antenna. Preferred embodiments of the present invention include multiple field generator coils and/or multiple sensor coils.

Each pair (i,j) of one field generator coil and one sensor coil will cause a different set of signals $s^k$, $s^l$ and $s^m$ to be generated by transponder 30 and measured by sensor circuits 28. Three such pairs will be sufficient to allow three sets of signals $s^k$, $s^l$ and $s^m$ to be measured for a given position and orientation of transponder 30, or nine signal values in all, provided that the vector field pairs, $h_i$ and $r_j$, are all linearly independent of one another. Referring to equation (1), it may be appreciated that these nine values are sufficient to fully determine the elements of matrix T using linear matrix computations.

When h, r and the translational position of the transponder are known, however, one such pair of a field generator coil and a sensor coil is sufficient to fully determine the rotational orientation of the transponder. In this case, the elements of matrix T are derived from only three independent variables, i.e., the angles of rotation of the transponder about its three axes. The orthonormality of matrix T, as expressed in equation (6) below, allows all nine of the matrix elements to be determined from these three angles. Preferably an iterative method of solution, such as the Newton-Raphson method, is used to calculate the three angles based on the measured signals due to the single pair of field generator coil and sensor coil.

In preferred embodiments of the present invention, there are a total of at least four field generator and sensor coils, whose respective vector fields h or r are mutually linearly independent, and thus, both the translational position and rotational orientation of the transponder are determined. In one such embodiment, there is one field generator coil and three sensor coils; in another such embodiment, there are three field generator coils and one sensor coil; and in a third such embodiment, there are two field generator coils and two sensor coils.

Other preferred embodiments of the invention, however, provide more than a total of four field generator and sensor coils, so as to improve the accuracy of determination of the position and orientation of object 22 or of multiple objects in the region of interest. One such preferred embodiment is illustrated schematically in FIG. 4, in which a field generator coil 80 and four sensor coils 82, 84, 86 and 88 are contained in a generally planar enclosure 90. For convenience, enclosure 90 is shown as transparent in FIG. 4, but it may be generally made of any transparent or opaque material that does not substantially affect the electromagnetic fields of the field generator 80 and transponder 30. The embodiment shown in FIG. 4 is particularly useful for determining the position and orientation of an object 22, to which transponder 30 is mounted, located in the space directly above enclosure 90.

Figure 4:
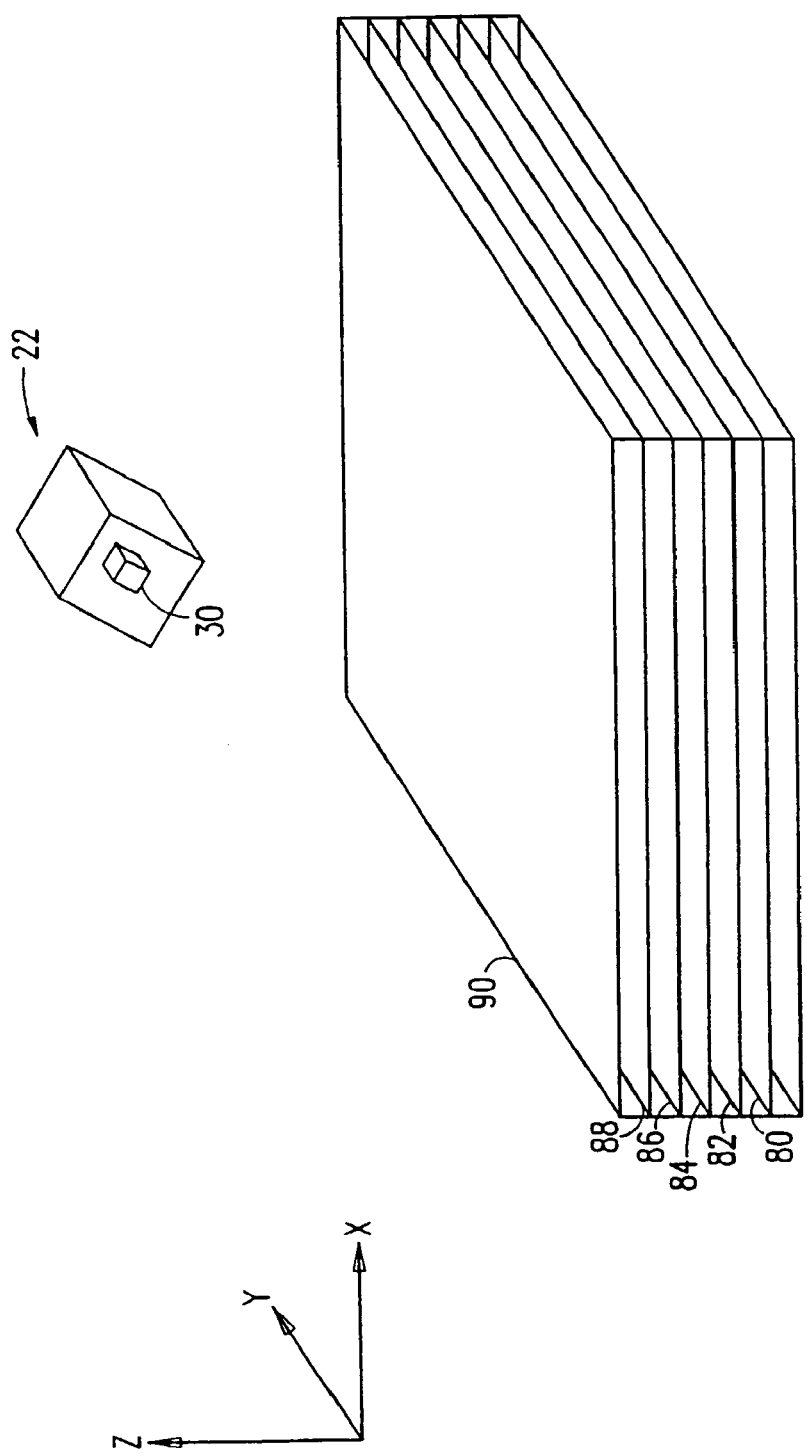
FIG. 4 is a preferred embodiment of the present invention having one field generator and four sensor coils.

In the embodiment shown in FIG. 4, sensor coils 82 and 84 are wound particularly so as to allow determination of the linear position of transponder 30 on object 22 in the X-direction, as shown in the figure, with high accuracy. Similarly, sensor coils 86 and 88 are wound so as to allow accurate determination of the Y-direction linear position. As provided by equation (1), however, the signals received by sensor coils are sufficient to determine the vertical (Z-direction) position and three-angle rotational orientation of the object.

Sensor coils 82, 84, 86 and 88 may preferably be constructed as shown in FIG. 5A. This figure shows a preferred embodiment of two sensors, identified here as left and right sensor coils 82 and 84 respectively. The figure and the following discussion thereof may equally be applied to coils 86 and 88, which are rotated 90° with respect to coils 82 and 84. FIG. 5B shows sub-coils of left sensor coil 82 separated for illustrative purposes.

Left sensor 82 is preferably a rectangular coil, preferably square coil of size L, including a plurality of sub-coils 102, 104, 106, etc., having a common length L but different widths. As shown in FIGS. 5A and 5B, the widths of sub-coils 102, 104, 106, etc., are S, 2S, 3S, etc, respectively up to L, which is the width of the widest sub-coil, labeled 108. The left sides of all the sub-coils of array 82 substantially overlap, while the right sides of consecutive sub-coils are separated by intervals of width S. Coil 82 comprises a serial connection of the sub-coils 102, 104, 106, up to 108.

Right sensor coil 84 is preferably a mirror image of left sensor coil 82. In right coil 84, the right sides of sub-coils 102, 104, 106, etc., substantially overlap, while the left sides of consecutive sub-coils are separated by intervals of length S. In both coils 82 and 84, interval length S is preferably smaller than the diameter of coils 32, 34, 36. The number of loops in each sub-coil is preferably substantially the same.

Figure 6A:
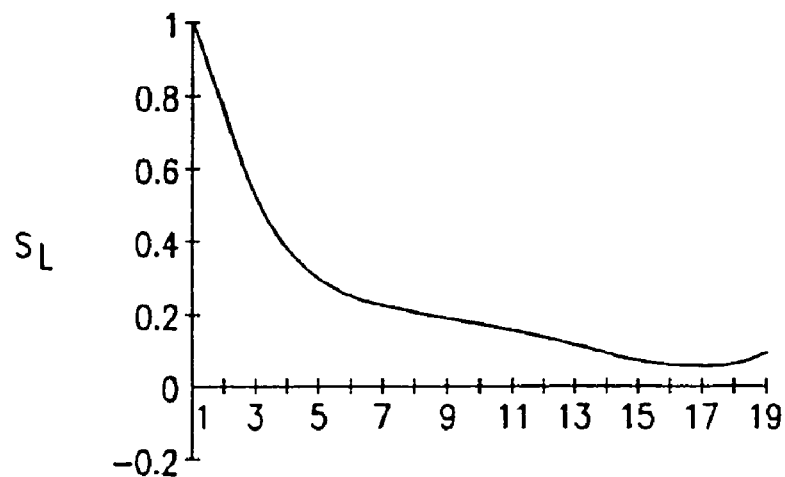
FIGS. 6A and 6B are schematic graphs of sensor signals, not necessarily exact, produced by the sensor array of FIG. 5A.
Figure 6B:
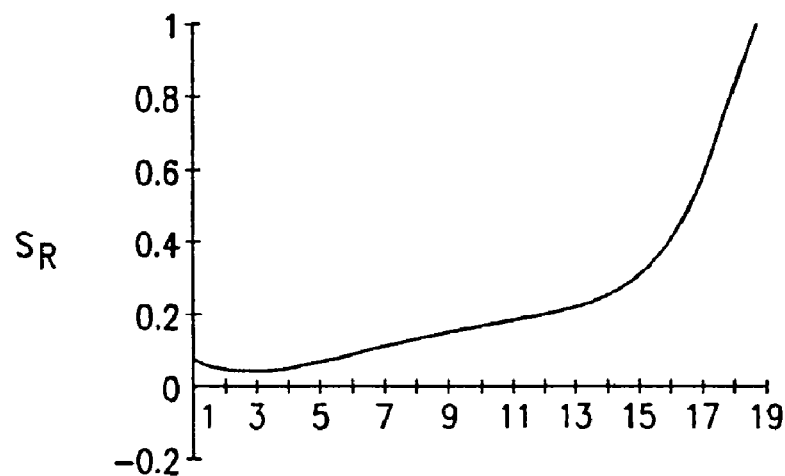

FIGS. 6A and 6B show the normalized amplitudes of total sensor signals $s_L$ and $s_R$, received by sensor coils 82 and 84 respectively in response to signals generated by a single one of the transponder coils 32, 34, 36, as a function of the position of transponder 30 along the surface of enclosure 90 from left to right in the direction marked X in FIG. 4, wherein the Z-position of the transponder is held constant. The functional dependence of the signals shown in FIGS. 6A and 6B is shown for purposes of illustration and is not necessarily exact. The dependence of the normalized sum of the signals received by sensor coils 82 and 84 from coils 32, 34 and 36 on the X-position of transponder 30 will be of substantially the same form, regardless of the transponder's orientation and Y- and Z-axis positions.

A further advantage of the preferred construction of coils 82 and 84, as shown in FIGS. 5A and 5B, is that the signal strengths received by the coils as a function of X-position are complementary, i.e., at the right end of the surface of enclosure 90, where $s_L$ is seen in FIG. 6A to be weak, $s_R$ can be seen to be strong in FIG. 6B, and vice versa. It will, therefore, be appreciated that with appropriate signal processing, for example by taking sums and differences of $s_L$ and $s_R$, improved signal-to-noise ratio may be achieved, without necessitating very wide dynamic range in the sensor circuitry.

It will be appreciated that FIGS. 5A, 5B, 6A and 6B have referred to left and right coils 82 and 84 only by way of example, and that everything said above in reference to this pair of coils is equally applicable to coils 86 and 88, which are rotated by 90° with respect to coils 82 and 84.

In preferred embodiments of the present invention, in accordance with FIGS. 4, 5A and 5B, sums and differences of the signals from left and right sensor coils 82 and 84 may be used to determine the X position of the transponder, as disclosed in PCT patent application number PCT/US95/10096 and incorporated herein by reference. Similarly, sums and differences of sensor coils 86 and 88 may be used to determine the Y position of the transponder.

Figure 7A:
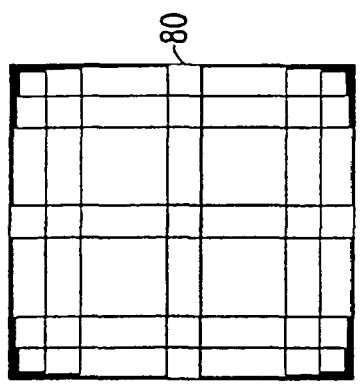
FIG. 7A is a schematic illustration of a preferred field generator coil for the embodiment of FIG. 4.
Figure 7B:
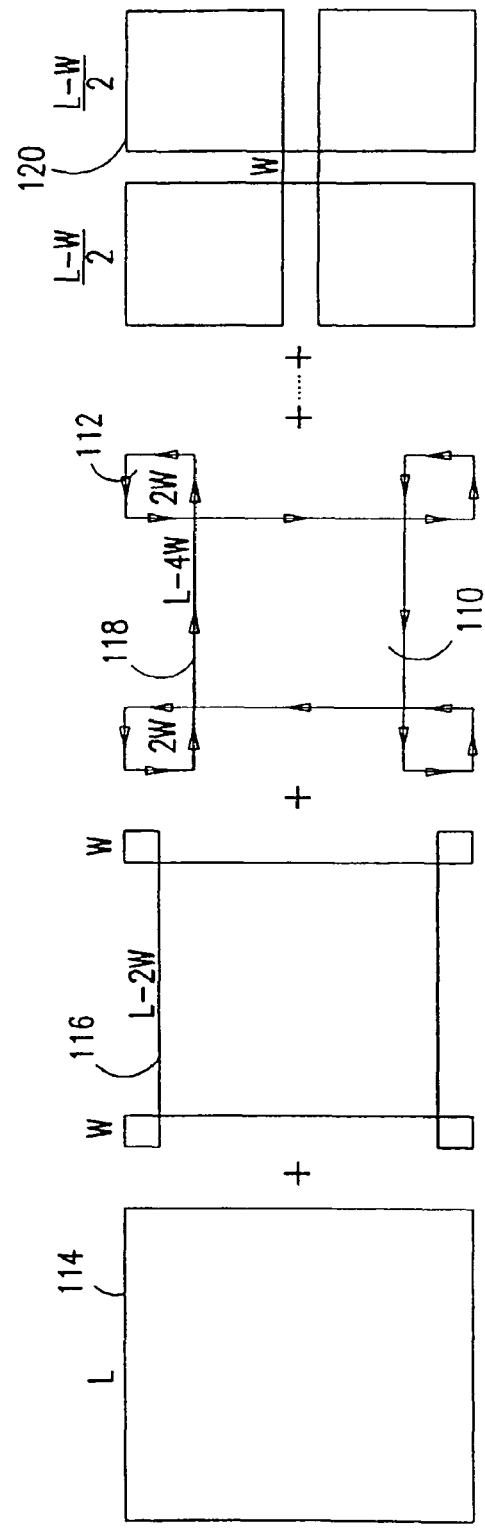
FIG. 7B is an exploded, explanatory illustration showing the construction of the excitation coil of FIG. 7A.

FIG. 7A illustrates the construction of field generator coil 80, which is particularly suitable for the preferred embodiment of FIG. 4, to be used in conjunction with the sensor coils shown in FIGS. 5A and 5B. FIG. 7B shows sub-coils of coil 80 separated for illustrative purposes. Coil 80 preferably includes a rectangular peripheral sub-coil 114, preferably a square having a side of length L, and a plurality of zoned sub-coils 116, 118 . . . 120. As shown schematically on sub-coil 118, each zoned sub-coil preferably includes five zones, namely, a center zone 110, in which current flow is in a first direction, and four corner zones 112, in which current flow is in a second direction opposite the first direction. The sides of corner zones 112 of sub-coils 116, 118, etc. are of dimension W, 2W, etc., respectively, and the sides of center zones 110 of sub-coils 116, 118, etc., are L−2W, L−4W, etc., respectively. The corner zones of the last sub-coil, labeled 120, have a side length of (L−W)/2. The number of loops in the different sub-coils are selected so as to generate electromagnetic fields above enclosure 90 that will cause the signal amplitudes received by sensor coils 82, 84, 86 and 88 from transponder coils 32, 34, 36, and then processed by taking sums and differences of coil pairs 82-84 and 86-88, to be substantially independent of the position of transponder 30 along the X- and Y-axes of FIG. 4.

For example, when L=19 and W=1, signal amplitudes that are substantially independent of the X- and Y-position of the transponder are obtained for the following numbers of loops: 100, 35, 31, 27, 22, 17, 13, 9, 6 and 2, starting from sub-coil 114 and going from left to right in FIG. 7B. This configuration provides an excitation field that is stronger in the center of the surface of enclosure 90 than at the edges, so as to compensate for the curves shown in FIGS. 6A and 6B, which show relatively greater signals at the edges. A greater or lesser number of sub-coils may be used, depending on the accuracy described.

Figure 7C:
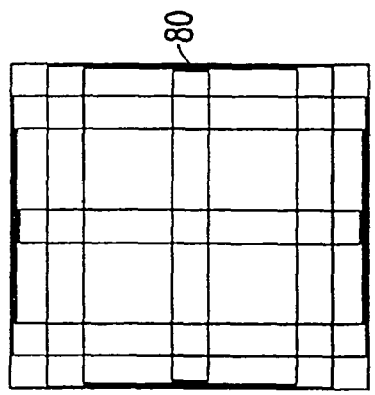
FIG. 7C is a schematic illustration of an alternative preferred field generator coil for the embodiment of FIG. 4.
Figure 7D:
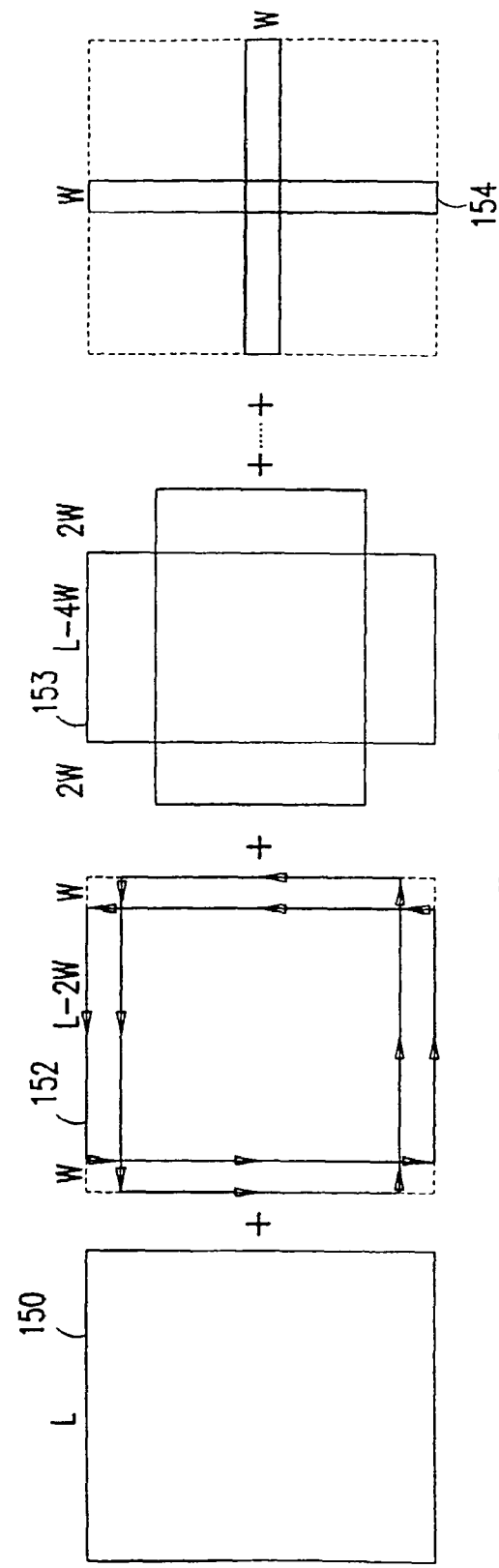
FIG. 7D is an exploded, explanatory illustration showing the construction of the excitation coil of FIG. 7C.

FIGS. 7C and 7D show an alternative preferred embodiment of field generator coil 80, where FIG. 7C shows the entire coil schematically, and FIG. 7D is an exploded view to show more clearly the structure of the coil. The embodiment of FIGS. 7C-D, like the embodiment of FIGS. 7A-7B, provides an excitation field that is stronger in the center of the surface of enclosure 90 than at the edges, so as to compensate for the curves shown in FIGS. 6A and 6B.

As shown in FIG. 7C, coil 80 is substantially square, with sides of length L. Coil 80 is made up of a succession of sub-coils 150, 152, up to 154, as shown in FIG. 7B. The first sub-coil 150 is substantially square, with sides of length L. The next sub-coil 152 comprises two rectangular loops arranged at right angles to one another, where two opposite sides of each rectangle are of length L, and the other two opposite sides are of length L−2W. The next sub-coil will comprise two rectangular loops, with sides of length L and L−4W. This progression of sub-coils continues to the last sub-coil 154, which comprises two rectangular loops with sides of length L and W.

The number of loops in the different sub-coils are selected so as to generate electromagnetic fields above enclosure 90 that will cause the signal amplitudes received by sensor coils 82, 84, 86 and 88 from transponder coils 32, 34, 36, and then processed by taking sums of coil pairs 82-84 and 86-88, to be substantially independent of the position of transponder 30 along the X- and Y-axes of FIG. 4.

For example, when L=19 and W=1, sum signal amplitudes that are substantially independent of the X- and Y-position of the transponder are obtained for the following numbers of loops: 24, 35, 31, 27, 22, 17, 13, 9, 6 and 2, starting from sub-coil 150 and going from left to right in FIG. 7D. This configuration provides an excitation field that is stronger in the center of the surface of enclosure 90 than at the edges, so as to compensate for the curves shown in FIGS. 6A and 6B, which show relatively greater signals at the edges. As in the preceding embodiment, a greater or lesser number of sub-coils may be used, depending on the accuracy desired.

Figure 8A:
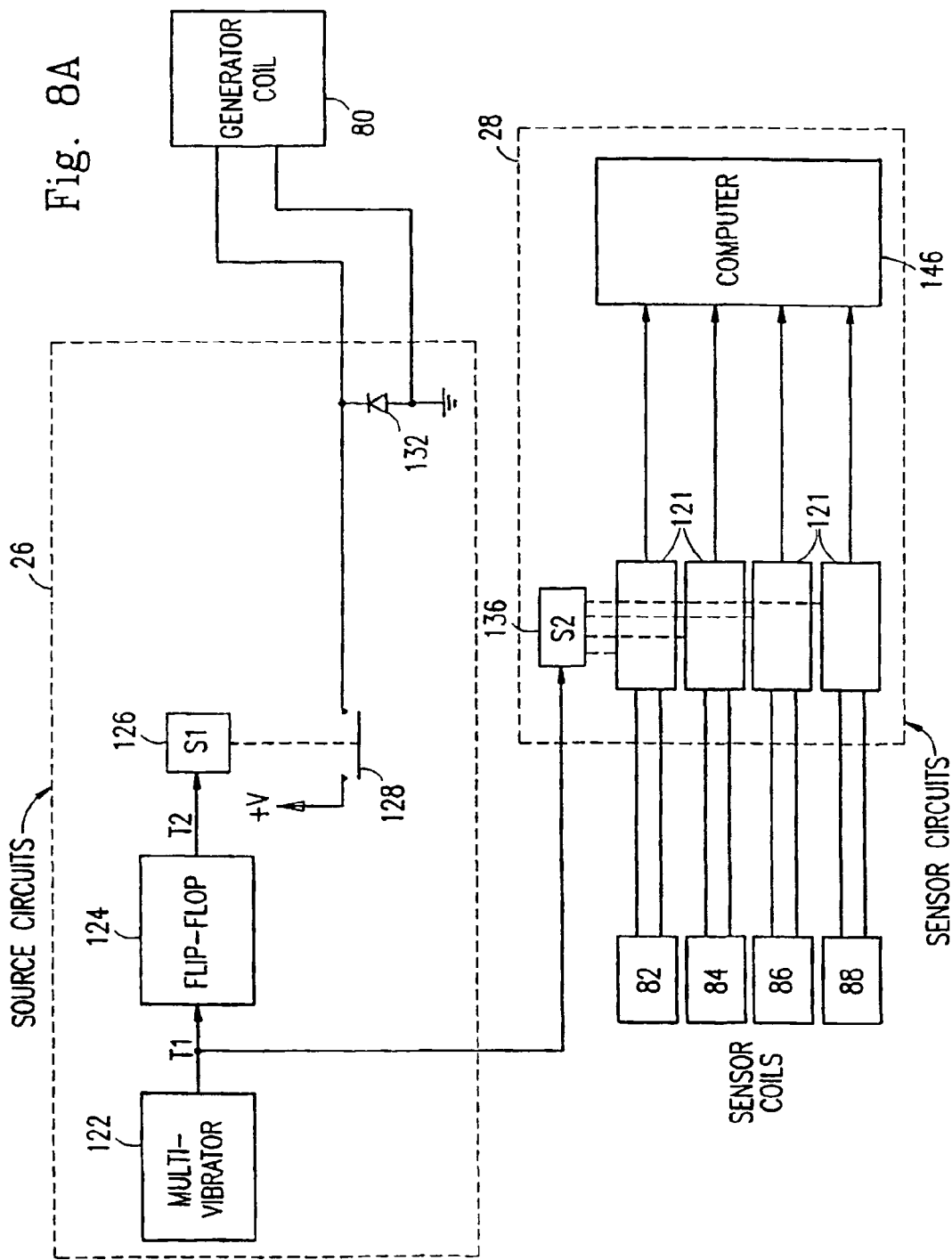
FIG. 8A is a schematic block diagram of circuitry useful for operating preferred embodiments of the present invention.
Figure 8B:
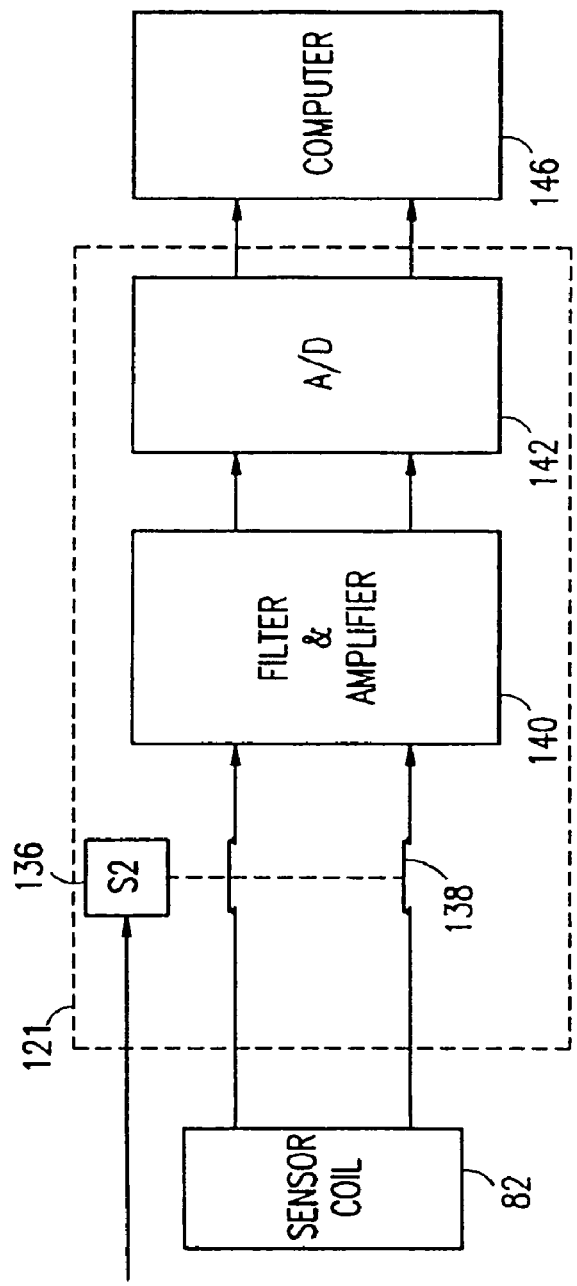
FIG. 8B is a schematic block diagram showing details of the sensor circuitry of FIG. 8A.

Preferred field generator circuitry 26 and sensor circuitry 28 is shown in FIGS. 8A and 8B. FIG. 8A shows the entire embodiment, while FIG. 8B shows signal processing circuitry 121 in detail. FIGS. 9A-9D schematically illustrate signals generated and received by the circuitry of FIG. 8. These signals are shown for purposes of illustration and are not necessarily exact. The following paragraphs refer to FIGS. 8 and 9, which are drawn and described here with reference to the field generator and sensor coils of the preferred embodiment of the invention shown in FIG. 5, but may equally be applied to any embodiment comprising one field generator coil and multiple sensor coils.

Source circuits 26 comprise a monostable multi-vibrator 122, which generates a time signal T1, preferably having a duty cycle of approximately 1:3 or higher, which is fed to a flip-flop 124. Multivibrator 122 is preferably triggered by an external synchronization signal. If synchronization is not required, then multivibrator 122 can be an astable multivibrator.

Figure 9A:
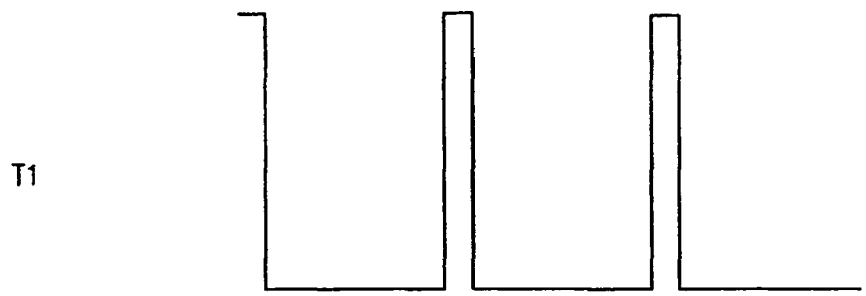
FIGS. 9A-9D are schematic graphs of signals, not necessarily exact, generated by the circuitry of FIG. 8.
Figure 9B:
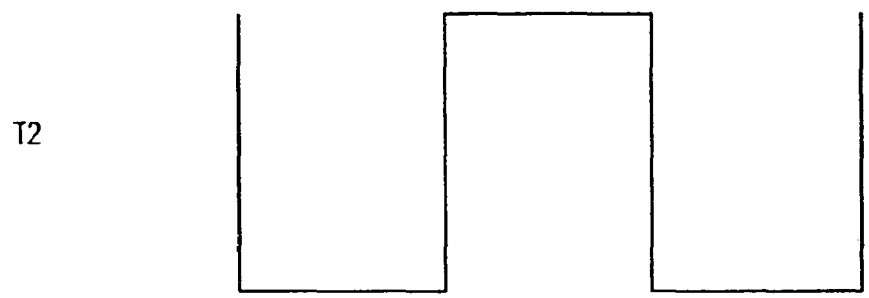
Figure 9C:

Flip-flop 124 converts signal T1 into a corresponding, alternating signal T2, preferably having a duty cycle of 1:1. When alternating signal T2 is at its higher value, a switch 126 is activated to close a contact 128 and, thereby, to drive current through field generator coil 80. When signal T1 is at its higher value, a switch 136 in sensor circuits 28 is activated to open contacts 138 in the signal processing circuits 121 and, thereby, to temporarily prevent sampling of signals. Sampling is prevented during these intervals so as to avoid the undesired effects of spikes generated by the sensor coils due to abrupt changes in the field generator current. The duty cycle of T1 is selected in accordance with the expected duration of such spikes. A typical sensor signal, with spikes, is shown in FIG. 9C.

When signal T2 is at its lower value, switch 126 opens contact 128, and remnants of the excitation signal are grounded through a diode 132.

Signals from sensor coils 82, 84, 86 and 88 are received by respective signal processing circuits 121. The preferred embodiment shown in FIG. 8A provides separate signal processing circuits 121 for each of the sensor coils, so as to achieve high data throughput. It will be appreciated, however, that in other preferred embodiments, multiple sensor coils may be coupled through a switch to a single processing channel, similar to circuits 121. In these embodiments, the sensor signals are processed sequentially, rather than in parallel.

Figure 9D:

FIG. 8B shows a more detailed block diagram of circuits 121, which are shown as being connected for example to one of the sensor coils, namely coil 82. Circuits 121 comprise an amplifier 140, which preferably includes an input filter. A typical signal amplified by amplifier 140 is shown in FIG. 9D. The amplified signals are then converted by an analog to digital (A/D) converter 142 to corresponding digital signals, which are fed to a processor (computer) 146. Processor 146 calculates the signal spectrum of the sensor signals, as described above, for each period of signal T2. The signals due to each of transponder circuits 38, 40, 42 are identified by the peaks at their respective resonant frequencies $\omega_k$, $\omega_l$, and $\omega_m$ in the calculated power spectrum. The amplitudes of the peaks $s^k$, $s^l$ and $s^m$ are used by processor 146 in accordance with equation (1) and computational methods that will be described below to determine the translational position and rotational orientation of transducer 30.

Processor 146 may be any processor known in the art that is capable of the calculations herein described, for example a personal computer. A/D converters 142 may include any A/D converters whose sampling rate is sufficient to distinguish between the different resonant frequencies $\omega_k$, $\omega_l$, and $\omega_m$.

In other preferred embodiments of the invention, field generator circuitry 26 may provide alternating current to the field generator coils 20, at the frequencies of the transponder coils. These current inputs may be continuous or pulsed, and will generally comprise a superposition of sinusoidal signals at the respective resonant frequencies $\omega_k$, $\omega_1$, and $\omega_m$ of the transponder coil circuits 38, 40 and 42.

In response to the electromagnetic fields generated by the field generator coils, transponder coils 32, 34 and 36 will generate signals at their resonant frequencies. These signals, however, will be 90° out of phase with the electromagnetic fields of the field generators. Sensor circuitry 28 is provided so as to separate the transponder signals from signals received by the sensors directly from the field generators, since the two signals are 90° out of phase.

Figure 10:
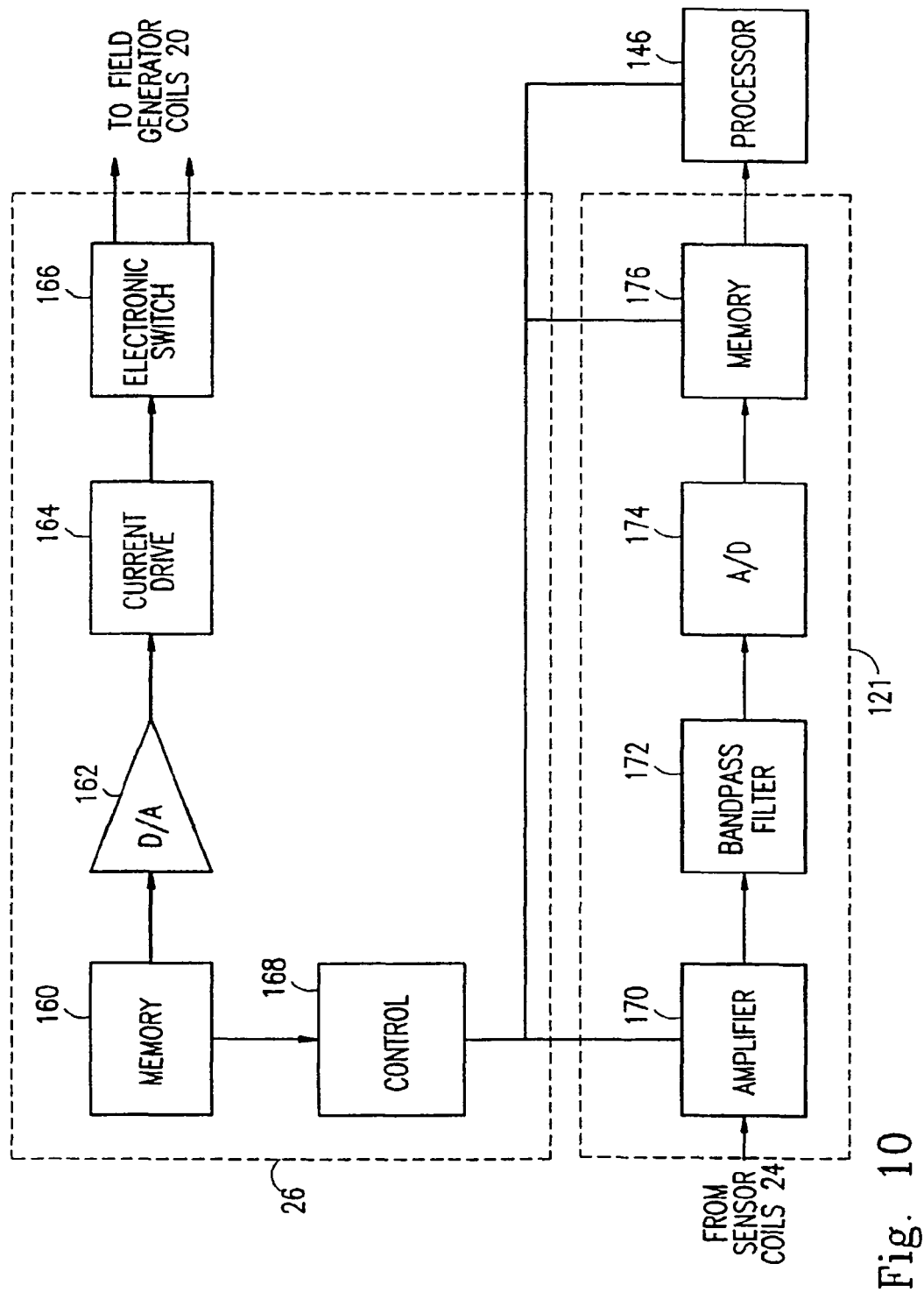
FIG. 10 is a schematic block diagram showing of circuitry useful for operating other preferred embodiments of the present invention.

FIG. 10 shows a preferred embodiment of source circuits 26, for use with alternating current inputs to field generator coils 20 as described above. FIG. 10 shows schematically only one output to a field generator coil 20 and a single input from a sensor coil 24 to a signal processing channel 121. It will be appreciated, however, that additional output and input channels of the types shown in FIG. 10 may be added in accordance with the number of field generator and sensor coils that are used.

Source circuits 26 in FIG. 10 comprise memory 160, in which a signal is stored in digital form comprising a vector superposition of the resonant frequencies of all the transponder circuits 38, 40 and 42. The signal stored in memory 160 is preferably of such length as to provide current input to field generator coil 20 of 4 msec duration. A digital-to-analog (D/A) converter 162 converts the signals stored in memory 160 to analog form. Current drive 164 amplifies the signals generated by converter 162 and thus furnishes the current input to coil 20. An electronic switch 166 is optionally provided, so that a single source circuit 26 may provide current input to several field generator coils in sequence. A controller 168 regulates the timing of the current input to the field generator, and also provides timing and phase signals to the signal processing circuits 121.

Sensor coil 24 receives the signals generated by transponder coils 32, 34, 36, along with signals at the same frequencies as those of the transponder coils, directly from the electromagnetic field generated by the field generator coils 20. As noted above, the transponder signals are substantially 90° out of phase with the signals due to the field generator coils. These signals are fed to amplifier 170 and filtered by band pass filter 172 to remove noise at frequencies above and below the transponder signal frequencies. The amplified and filtered signals are converted to digital form by A/D converter 174. The digitized signals are then stored in memory 176.

Processor 146 reads the digitized signals from memory 176 and separates the transponder signals from the background signals due to the electromagnetic field generator on the basis of their known phases. Preferably this separation is performed by vector multiplication of the signals by an appropriate normalized signal that is 90° out of phase with the field generators, to yield the scalar product of the two vectors. Multiplication is preferably performed after transformation of the signals to the frequency domain and calculation of sine and cosine coefficients by means of a discrete Fourier transform.

When the coils shown in FIGS. 4, 5A and 5B are used, if the signals from coils 82 and 84 are summed together, the resultant sum signal is 90° out of phase with the background signals due to direct reception from the electromagnetic field generators, independent of the position of the transponder. This sum signal may thus be normalized and used in vector multiplication with the difference signal that is obtained by subtracting the signals received from coils 82 and 84, to separate the transponder signals from the background. This procedure removes difference signal components that are in phase with the field generators, due to parasitic transmissions from the sensor coils. It may be applied, as well, to the difference signal from coils 86 and 88. The procedure may similarly be used to remove such parasitic components when they are encountered in embodiments using pulsed excitation of the field generators, such as that shown in FIG. 8.

In preferred embodiments of the present invention, one or more of the field generator coils may also serve as sensor coils. Thus, embodiments of this type may be constructed using only two or three of such dual-purpose field generator and sensor coils to fully determine the position and orientation of the object.

Figure 11:
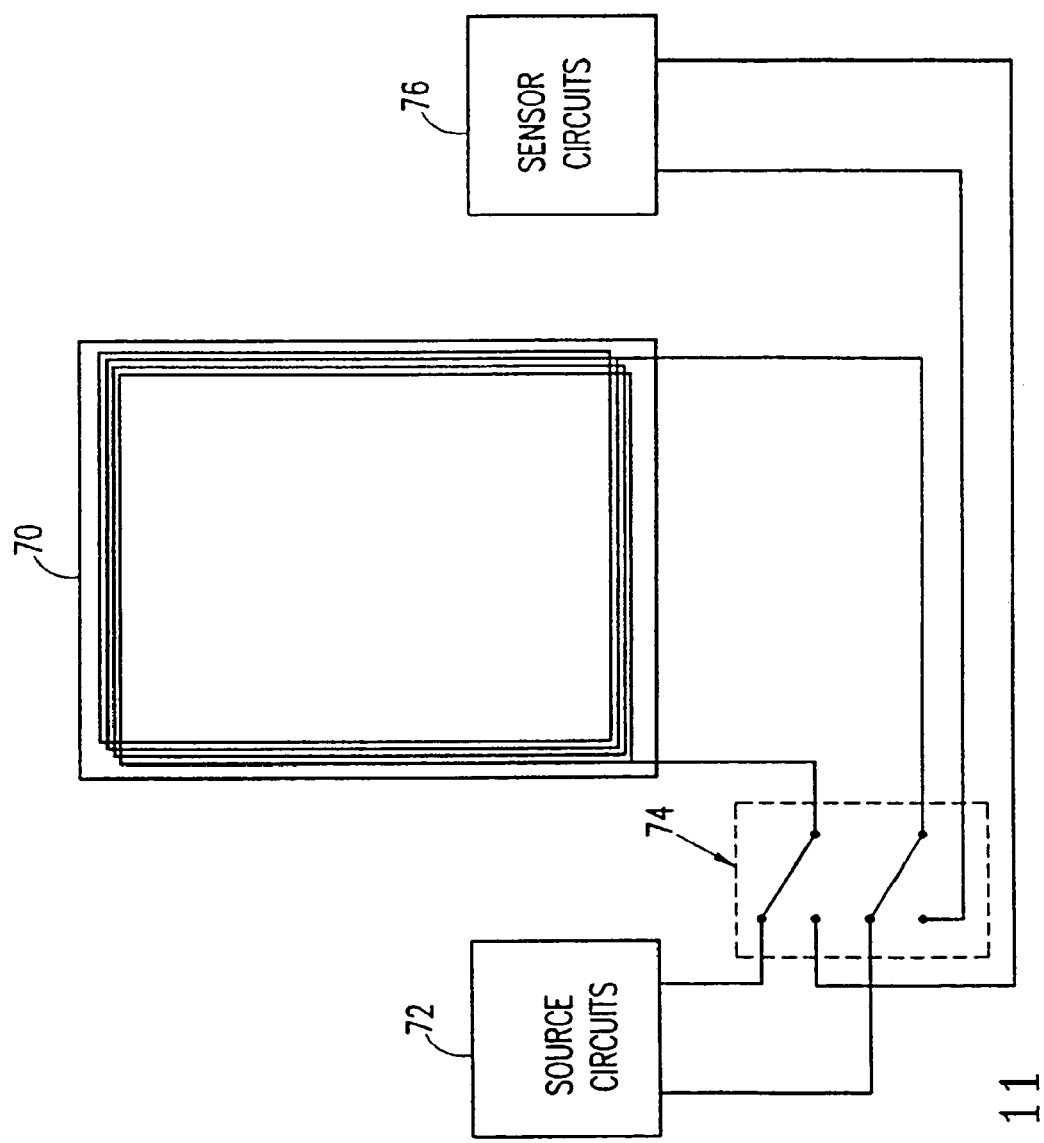
FIG. 11 is a schematic illustration of a coil that serves as both a field generator and a sensor.

FIG. 11 shows an illustration of a preferred embodiment of such a dual-purpose field generator and sensor coil 70. Source circuit 72 provides an electrical current to coil 70 through switch 74, for the purpose of generating the desired electromagnetic field. Switch 74 then switches the connection of coil 70 to sensor circuit 76. Transponders 30 continue to resonate at their characteristic frequencies after the coil's electromagnetic field has been switched off. This continuing resonance generates signals, which are sensed by coil 70 and detected by sensor circuit 76.

Figure 12:
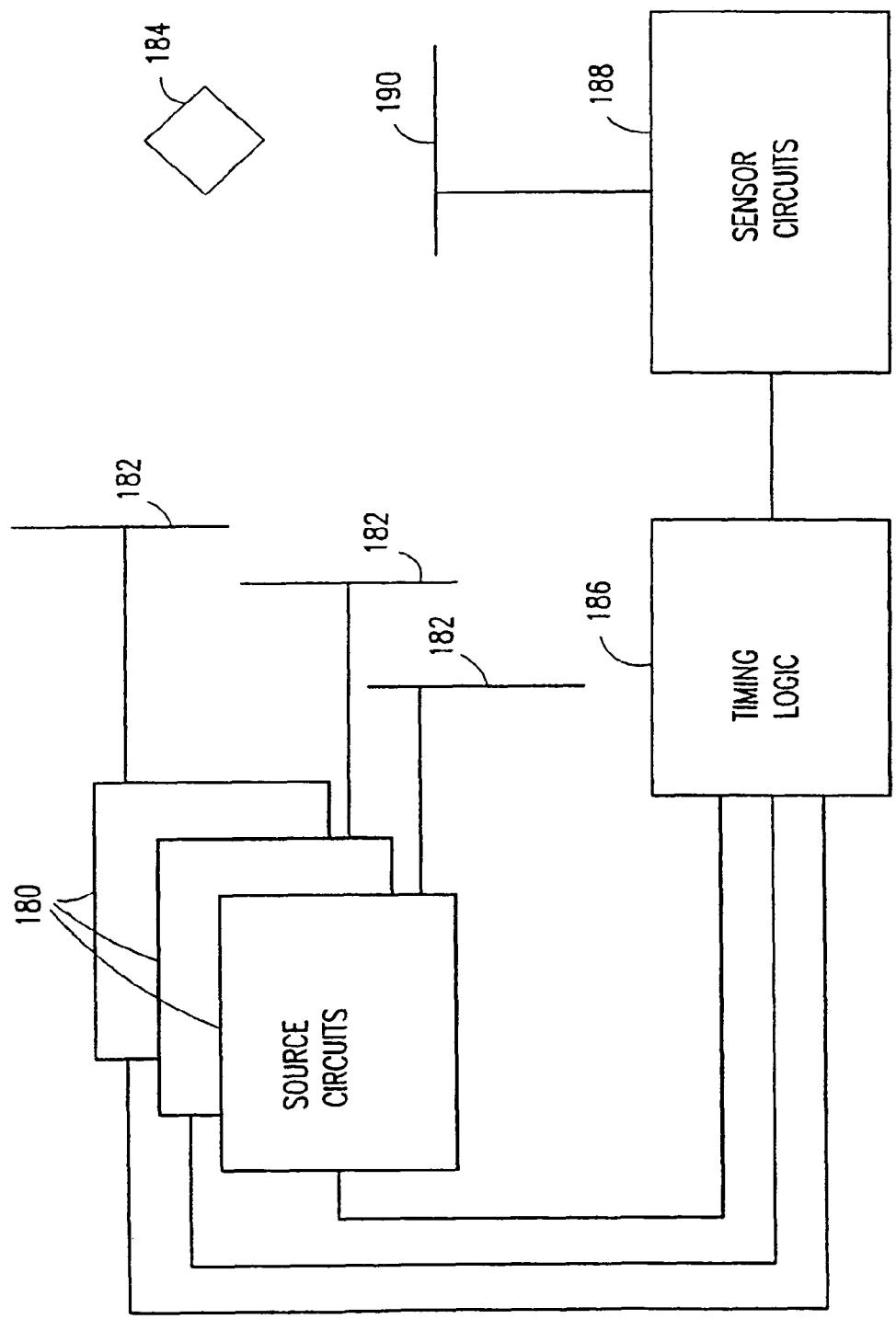
FIG. 12 is a schematic illustration of a preferred embodiment of the invention having multiple field generator coils.

Another preferred embodiment of the invention is geometrically constructed in substantially the same way as the preceding embodiment described with reference to FIG. 4, but differs from the preceding embodiment in that coils 82, 84, 86 and 88 are used as field generator coils, while coil 80 is used as a sensor coil. In this and other preferred embodiments of the present invention having more than one field generator coil, it is generally necessary for sensor circuits to distinguish among the signals generated by the transponders according to which one of the multiple field generator coils caused the signal to be generated. FIG. 12 illustrates a preferred embodiment of the invention wherein timing logic is used to trigger multiple field generator coils, so that sensor circuits may distinguish among the transponder signals according to the time at which they were received.

As shown in FIG. 12, multiple source circuits 180 provide electrical current pulses to multiple field generator coils 182, which generate electromagnetic fields in the vicinity of transponder 184. In alternative embodiments of the invention, a single source circuit is coupled by a switch to coils 182, and the switch applies the electrical current pulses of the source circuit to each of the coils in sequence. Source circuits 180 and sensor circuits 188 are preferably similar to those shown in FIG. 8A, and generate current pulses of the type shown in FIGS. 9A-9B. Referring again to FIG. 8A, timing logic 186, provides trigger pulses to multivibrators 122 in sequence, causing source circuits 180 supply current pulses to coils 182 in succession, so that field generator coils 182 generate fields one after another without overlap. Sensor circuits 188 receive signals sensed by sensor coils 190. Timing logic 186 also provides trigger and logic outputs to sensor circuits 188, so as to operate switch 136 and indicate to computer 146 which of the multiple field generator coils 182 is operating. Thus, computer 146 identifies and processes separately the signals received due to each of the multiple field generator coils 182.

In all preferred embodiments of the present invention, computer circuitry 146, as shown in FIG. 8A, applies matrix computations to the signal amplitudes measured by sensor circuits 28, so as to determine the position and orientation of transponders 30. Equation (4) above presents the form of one such matrix computation that is preferably used to determine the translational position of the transponder.

In a preferred embodiment of the present invention, the rotational orientation of the transponder is likewise calculated using linear matrix operations. For the k axis of the transponder, we may write the first line of equation (1) for each generator-sensor coil pair:

$$s^k = p \underline{r} T^t \begin{pmatrix} g_k \\ 0 \\ 0 \end{pmatrix} = pg_k(r_x T_{11} + r_y T_{12} + r_z T_{13}) \quad (5)$$

where $$g_k = T_{11} h_x + T_{12} h_y + T_{13} h_z$$

In a preferred embodiment of the invention having at least two sensor coils, and in which $\underline{r}$, $\underline{h}$ and the transponder's translational position are known or determined using methods described above, two signals $s_1^k$ and $s_2^k$ are measured, so that two sets of independent coefficients for $T_{11}$, $T_{12}$, $T_{13}$ are obtained for use in calculating equation (5). Taken together with the orthonomality condition for Euler transformations, which provides that $$T_{11}^2 + T_{12}^2 + T_{13}^2 = 1 \quad (6)$$

these two sets of independent coefficients are then sufficient to fully determine $T_{11}$, $T_{12}$ and $T_{13}$. The elements of the second and third rows of matrix T are similarly determined using the signals measured due to axes l and m of the transponder.

In other preferred embodiments of the present invention having at least three sensor coils, it is sufficient to know the response fields r of the sensor coils in order to fully determine the elements of matrix T. The electromagnetic field h due to field generator 22 need not be known. In this case we use the three signals $s_1^k$, $s_2^k$ and $s_3^k$ in equation (5), along with the orthonormality condition of equation (6), to calculate $T_{11}$, $T_{12}$ and $T_{13}$. The l- and m-axis transponder signals are similarly used to calculate the elements of the second and third rows of T.

In other preferred embodiments having three or more field generator coils, the following equation, derived from equation (1), is used to calculate the elements of matrix T:

$$s^k = p(g_k 0\ 0) T \underline{h} = pg_k(T_{11} h_x + T_{12} h_y + T_{13} h_z) \quad (7)$$

where now $$g_k = r_x T_{11} + r_y T_{12} + r_z T_{13}$$

It may be appreciated that in preferred embodiments having three or more field generator coils, only the respective fields $\underline{h}$ need be known, and not the response field $\underline{r}$ of the sensor coil or coils.

In other preferred embodiments of the invention having two field generator coils and two sensor coils, both $\underline{h}$ and $\underline{r}$ must be determined in order to calculate T.

There are, in fact, four valid solutions for matrix T according to equation (1), reflecting the fact that rotating a transponder coil by 180° does not alter either the magnitude or the phase of the signal measured by the sensors. Hence, the system described in accordance with the preferred embodiments above is limited to rotation within a portion of a sphere. Therefore, in preferred embodiments of the invention, the ambiguity-free segment of rotations is chosen by appropriately orienting the initial directions of the axes of the transponder coils. For example, in the preferred embodiment shown in FIG. 4, if one transponder coil axis is initially oriented along the X-axis, while the other two transponder coil axes are oriented in the Y-Z plane, at 45° angles to the X-Y plane, the object may then rotate freely through 360° in azimuth and ±90° of elevation, while being limited to ±45° of roll. The range of the azimuth and elevation includes all possible values of these two angles, while the roll is limited to the relevant portion of the sphere. These limitations are adequate for most known object tracking applications.

In an alternative preferred embodiment of the invention, for applications in which full spherical orientation determination is required, two transponders are fixed to the object, and the signals they generate are used jointly to track the rotational orientation of the object.

Although the above preferred embodiments of the invention have been described with reference to linear matrix calculations for determination of the position and orientation of transponder 30, it will be appreciated that other mathematical methods known per se in the art, including non-linear methods such as the Newton-Raphson method, may be used for this purpose.

In preferred embodiments of the present invention transponders may be attached to game pieces or toy figures for use in interactive computer games, such as those described in PCT patent application number PCT/US95/10096, referred to above.

Transponders in accordance with the present invention may also be fastened to a person's hand or to movable control objects, for use in actuating remote systems by sensing the motion of the hand or control objects.

Figure 13:
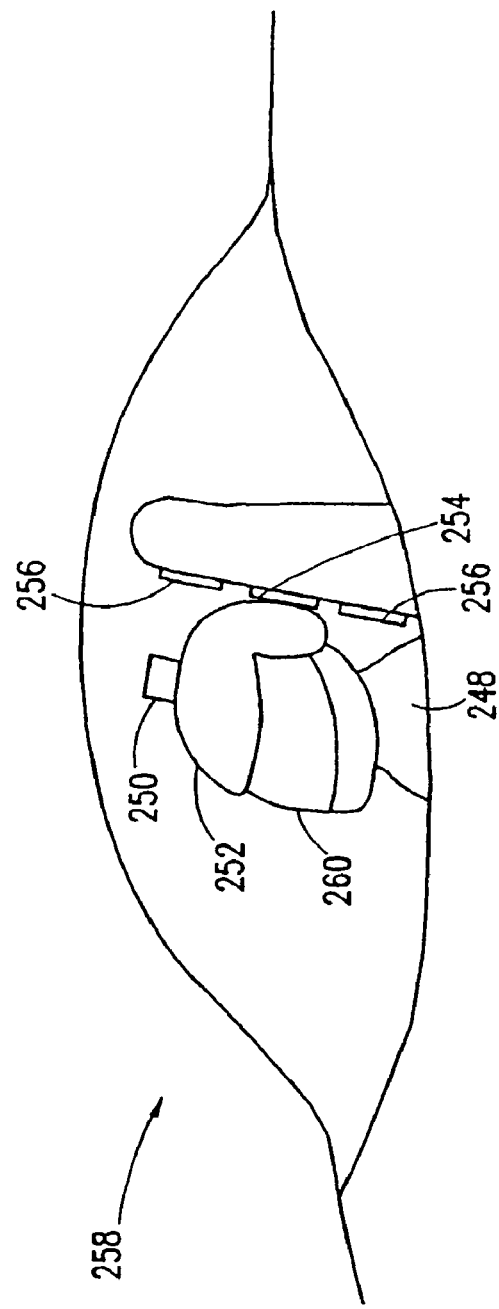
FIG. 13 is a schematic illustration of a preferred embodiment of the present invention for use in helmet tracking.

Other preferred embodiments of the present invention may be used to track the position and orientation of a helmet, which may be worn by a pilot 248 in an aircraft. One such embodiment is shown in FIG. 13, in which a transponder 250 is mounted on or inside a helmet 252, and one or more field generator coils 254 and sensor coils 256, in accordance with preferred embodiments of the present invention, are mounted in the cockpit 258. The helmet position and orientation data provided by the tracking system is used to aim the aircraft's weapons and/or to vary the pilot's helmet-mounted display 260.

Similarly, a helmet tracker based on the present invention may be used to provide a determination of the position and orientation of the head for use in virtual reality displays, simulation training and games.

It will be appreciated that these applications are presented here only by way of example, and that the present invention will be useful in a wide range of other applications.

The invention claimed is:

1. A method of tracking translation and rotation of one or more objects within a region of interest, comprising:

providing a passive transponder in the region of interest, the transponder having a position and an orientation;

generating an electromagnetic field in the region of interest, thereby causing the transponder to transmit electromagnetic signals;

mapping said electromagnetic field and said signals as functions of the position and the orientation of the transponder;

fixing the transponder to the object being tracked;

receiving the signals transmitted by the transponder while the transponder is fixed to the object being tracked; and processing the signals, with reference to said functions, to compute the three-dimensional translational position and three-axis rotational orientation of the object.

2. The method of claim 1, wherein the receiving is effected using at least one sensor separate from the transponder.

* * * * *